US009002863B2

(12) United States Patent
Faughnan

(10) Patent No.: US 9,002,863 B2
(45) Date of Patent: Apr. 7, 2015

(54) METHOD, APPARATUS AND COMPUTER PROGRAM PRODUCT FOR PROVIDING A RATIONAL RANGE TEST FOR DATA TRANSLATION

(75) Inventor: John Faughnan, Saint Paul, MN (US)

(73) Assignee: McKesson Financial Holdings, Hamilton (BM)

( * ) Notice: Subject to any disclaimer, the term of this patent is extended or adjusted under 35 U.S.C. 154(b) by 474 days.

(21) Appl. No.: 12/568,414

(22) Filed: Sep. 28, 2009

(65) Prior Publication Data

US 2011/0078164 A1 Mar. 31, 2011

(51) Int. Cl.
*G06F 17/30* (2006.01)
*G06F 19/00* (2011.01)

(52) U.S. Cl.
CPC .......... *G06F 19/3487* (2013.01); *G06F 19/322* (2013.01)

(58) Field of Classification Search
USPC ............................................ 707/756; 706/54
See application file for complete search history.

(56) References Cited

U.S. PATENT DOCUMENTS

| 2003/0195774 | A1* | 10/2003 | Abbo ................................ 705/3 |
| 2005/0210005 | A1* | 9/2005 | Thompson et al. ............... 707/3 |
| 2011/0071376 | A1* | 3/2011 | McKenna ..................... 600/336 |

FOREIGN PATENT DOCUMENTS

WO    WO 2006/086181    *  9/2006    .............. G06F 19/00

OTHER PUBLICATIONS

Sun, Jennifer Y., et al.; "A System for Automated Lexical Mapping"; *Journal of the American Medical Informatics Association;* vol. 13, No. 3; May/Jun. 2006; pp. 334-343.

* cited by examiner

*Primary Examiner* — Usmaan Saeed
*Assistant Examiner* — Jagdish Pandya
(74) *Attorney, Agent, or Firm* — Alston & Bird LLP

(57) ABSTRACT

A method for providing a data translation may include receiving an input string comprising a free text response indicative of a physiologic condition, and applying a selected transform to the input string to transform the input string into a translated value indicative of a value associated with the physiologic condition for storage in a fact repository. The selected transform may be selected from a library of potential transforms based on results of the selected transform relative to a rational range associated with the physiologic condition. A corresponding computer program product and apparatus are also provided.

14 Claims, 3 Drawing Sheets

METHOD, APPARATUS AND COMPUTER PROGRAM PRODUCT FOR PROVIDING A RATIONAL RANGE TEST FOR DATA TRANSLATION

TECHNOLOGICAL FIELD

Embodiments of the present invention relate generally to health care management solutions and, more particularly, relate to a rational range test for data translation.

BACKGROUND

For many years, the mechanism for evaluating clinical processes related to a particular patient has been the medical chart or medical record. As such, for example, the medical record has been used to record patient identification, health history, medical examination and/or lab test results, medical prescriptions and other information such as, for example, orders related to the particular treatments or diagnoses associated with the patient. Accordingly, in order to assess whether a patient has received or is due to receive a particular treatment or care related event, the patient's chart would typically be reviewed.

Recently, efforts have been made to move to electronic medical records (EMR). Although the EMR concept has encountered many issues in relation to, for example, cost, security, interoperability, etc., many hospitals are either employing, or planning to employ, some form of EMR. With clinical documentation systems moving to electronic media, clinical data may be available for incorporation into a number of different applications designed to assist in the management or use of such data. Computerized provider order entry (CPOE) is one example of a development that may improve the ability to electronically access information related to physician's orders. Many other applications are being developed to utilize electronic information on people and processes to manage the provision of various aspects of patient care including the provision of predictive care.

As the availability of electronic clinical data is increasing, the demand for applications that utilize such data to provide information, guidance and services is also increasing. Since many applications will require access to up to date or current care related information, the mechanism by which current and accurate information is provided to a variety of applications may become an important aspect in providing quality care management. Given that data entry can follow different protocols at different locations and in different organizations, and further given that some errors may be encountered that make that data "noisy", the translation of raw data into a useful and reliable repository of information may prove to be a challenge.

Accordingly, it may be desirable to provide an improved mechanism by which clinical data may be translated into a repository of information that is useful for addressing some of the challenges described above.

BRIEF SUMMARY

A method, apparatus and system are therefore provided to enable the provision of a rational range test for data translation. In this regard, for example, a rational range test may be applied to generate a transform rule for transforming data being provided for storage in a fact repository. The rational range test may, in at least one example, translate incoming data into a consistent form via selection of a transformation rule, from among a library of transformation rules, that is determined to provide good results for the transformation relative to other potential rules in the library.

In one exemplary embodiment, a method for providing a rational range test for data translation is provided. The method may include receiving an input string comprising a free text response indicative of a physiologic condition, and applying a selected transform to the input string to transform the input string into a translated value indicative of a value associated with the physiologic condition for storage in a fact repository. The selected transform may be selected from a library of potential transforms based on results of the selected transform relative to a rational range associated with the physiologic condition.

In another exemplary embodiment, a computer program product for providing a rational range test for data translation is provided. The computer program product may include at least one computer-readable storage medium having computer-executable program code instructions stored therein. The computer-executable program code instructions may include program code instructions for receiving an input string comprising a free text response indicative of a physiologic condition, and applying a selected transform to the input string to transform the input string into a translated value indicative of a value associated with the physiologic condition for storage in a fact repository. The selected transform may be selected from a library of potential transforms based on results of the selected transform relative to a rational range associated with the physiologic condition.

In another exemplary embodiment, an apparatus for providing a rational range test for data translation is provided. The apparatus may include processing circuitry. The processing circuitry may be configured for receiving an input string comprising a free text response indicative of a physiologic condition, and applying a selected transform to the input string to transform the input string into a translated value indicative of a value associated with the physiologic condition for storage in a fact repository. The selected transform may be selected from a library of potential transforms based on results of the selected transform relative to a rational range associated with the physiologic condition.

BRIEF DESCRIPTION OF THE SEVERAL VIEWS OF THE DRAWING(S)

Having thus described embodiments of the invention in general terms, reference will now be made to the accompanying drawings, which are not necessarily drawn to scale, and wherein:

DETAILED DESCRIPTION

Figure 1:
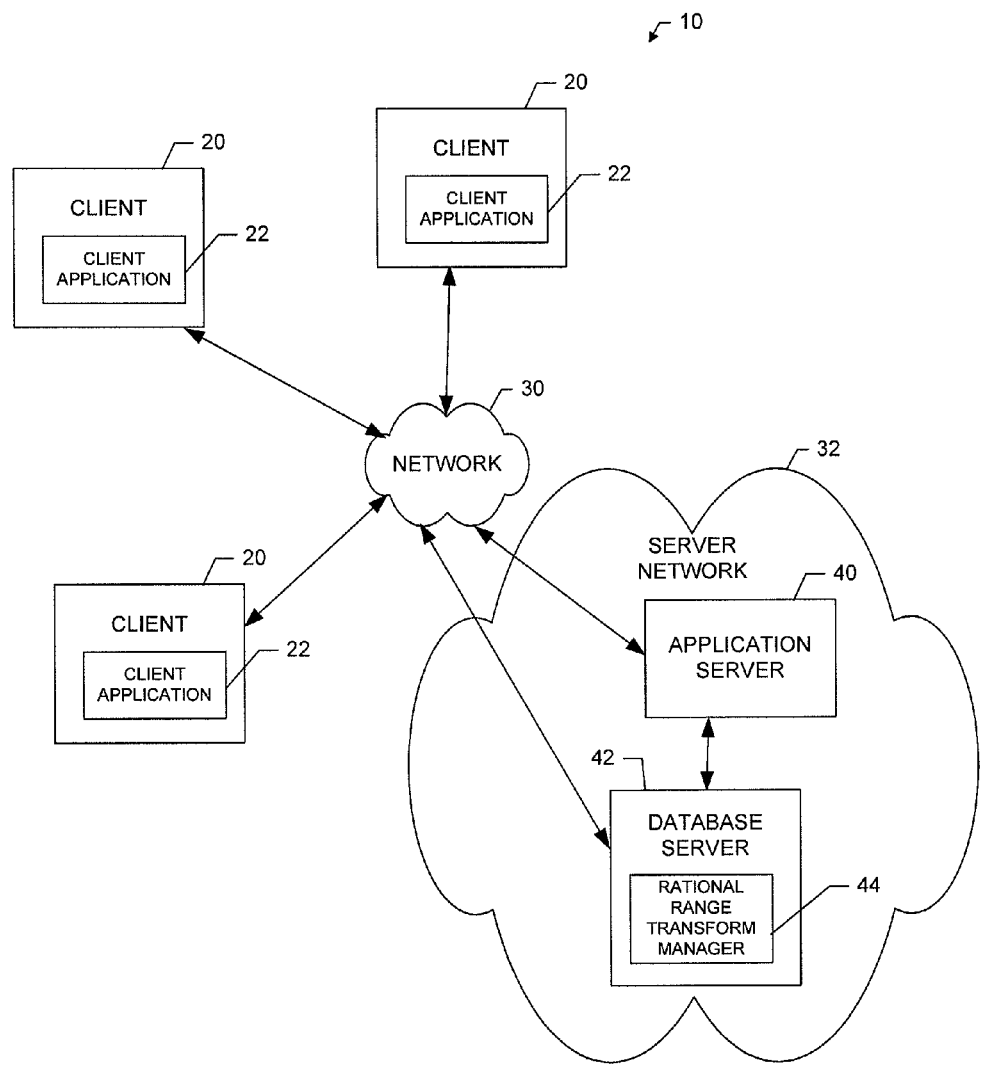
FIG. 1 is a block diagram illustrating a system for providing a reliable a rational range test for data translation according to an exemplary embodiment of the present invention.

Embodiments of the present invention will now be described more fully hereinafter with reference to the accompanying drawings, in which some, but not all embodiments of the invention are shown. Indeed, embodiments of the invention may be embodied in many different forms and should not be construed as limited to the embodiments set forth herein;

rather, these embodiments are provided so that this disclosure will satisfy applicable legal requirements. Like reference numerals refer to like elements throughout.

As indicated above, embodiments of the present invention are aimed at providing a mechanism by which a useful and reliable fact repository may be provided. In order to provide such a fact repository, embodiments of the present invention may provide a rational range test for enabling the generation of transform rules for use in data translation of incoming data so that the data stored in the fact repository is more likely to be accurate and useful information in an appropriate form for consumption by users and other applications alike.

An exemplary embodiment of the invention will now be described in reference to FIG. 1, which illustrates an exemplary system 10 in which an embodiment of the present invention may be employed. As shown in FIG. 1, a system according to an exemplary embodiment may include one or more clients 20 that may, in some cases, be associated with different corresponding units, wings or departments of a hospital or healthcare system. For example, one client 20 may be associated with a first hospital unit (e.g., an intensive care unit (ICU)) and a second client 20 may be associated with a second hospital unit (e.g., a respiratory therapy unit). However, information associated with multiple units may alternatively be accessible via a single client. Furthermore, in some cases, multiple clients may be associated with the same unit. In some examples, clients 20 could be located at nurse's stations, at various locations in hallways within a treatment unit, at a data entry location or even within patient rooms.

Each client 20 may be, for example, a computer (e.g., a personal computer, laptop computer, network access terminal, or the like) or may be another form of computing device (e.g., a personal digital assistant (PDA), cellular phone, or the like) capable of communication with a network 30. As such, for example, each client 20 may include (or otherwise have access to) memory for storing instructions or applications for the performance of various functions and a corresponding processor for executing stored instructions or applications. Each client 20 may also include software and/or corresponding hardware for enabling the performance of the respective functions of the clients as described below. In an exemplary embodiment, one or more of the clients 20 may include a client application 22 configured to enable one or more of various functions including, for example, data entry, information consumption, application execution, and/or the like. In this regard, for example, the client application 22 may include software for enabling a respective one of the clients 20 to communicate with the network 30 for the provision of and receipt of information associated with providing a patient care. As such, for example, the client application 22 may include corresponding executable instructions for configuring the client 20 to provide corresponding functionalities for the provision of and receipt of information associated with receiving patient care data, processing patient care data and/or providing patient care data as described in greater detail below. Moreover, in an exemplary embodiment, the client application 22 may include functionality, either alone or in cooperation with other applications and/or processing devices, for providing a rational range test for data translation.

The network 30 may be a data network, such as a local area network (LAN), a metropolitan area network (MAN), a wide area network (WAN) (e.g., the Internet), and/or the like, which may couple the clients 20 to devices such as processing elements (e.g., personal computers, server computers or the like) or databases. Communication between the network 30, the clients 20 and the devices or databases (e.g., servers) to which the clients 20 are coupled may be accomplished by either wireline or wireless communication mechanisms and corresponding protocols. In an exemplary embodiment, the network 30 may include or otherwise be embodied as a communication bus, such as an enterprise service bus, to which various clients 20, computers, databases, servers or other like devices may be operably connected.

In an exemplary embodiment, one of the devices to which the clients 20 may be coupled via the network 30 may include one or more application servers (e.g., application server 40), and/or a database server 42, which together may form respective elements of a server network 32. Although the application server 40 and the database server 42 are each referred to as "servers", this does not necessarily imply that they are embodied on separate servers or devices. As such, for example, a single server or device may include both entities and the database server 42 could merely be represented by a database or group of databases physically located on the same server as the application server 40. The application server 40 and the database server 42 may each include hardware and/or software for configuring the application server 40 and the database server 42, respectively, to perform various functions. As such, for example, the application server 40 and the database server 42 may each include respective processing logic and memory enabling the application server 40 and the database server 42 to access and/or execute stored computer readable instructions for performing various functions. In an exemplary embodiment, one function that may be provided by the database server 42 may be the provision of a rational range test for data translation to the clients 20. In this regard, for example, the database server 42 may include a rational range transform manager 44 comprising stored instructions for listening (e.g., via the enterprise service bus) for data being provided to the network (e.g., via clients 20) and determining what form of transformation to apply to the data so that the data can be stored in the database server 42 for use by other applications of the application server 40 or for access by the clients 20.

Additionally or alternatively, the application server 40 may be configured to enable the clients 20 to provide information to the application server 40, for use by the application server 40 in producing, maintaining and/or supplying patient care information. In this regard, for example, the application server 40 (or servers) may include particular applications related to various different electronic medical record modules (e.g., CPOE or others). As such, some application servers may host data entry mechanisms that enable the entry of patient information, treatment information, test results, medical history, orders, medications, observations, and numerous other types of information for storage in the database server 42. The database server 42 may therefore form a fact repository to accept core clinical data updates of observations, medication administrations, intravenous (IV) administrations, orders and other similar data that may be provided in the context of an EMR or other hospital or healthcare system electronic data gathering and/or storage regimes. However, as indicated above, the data to be stored in the fact repository may first be translated as appropriate by a translation layer that may include a mapping layer and a transform layer. The transform layer may include at least the rational range transform manager 44 configured to generate one or more transform rules via a rational range test so that the transform rules can be applied to data that is to be translated prior to storage in the fact repository.

In one embodiment, the fact repository may enhance patient data through associations with clinical concepts to form structured data. As a result of the associations with clinical concepts, the fact repository, which may in some cases include a processor and memory for enabling processing and storage, may process the patient data in various manners, such as by transforming the patient data to a standard representation. For example, in instances in which the data represents the patient's temperature, the fact repository may be configured (e.g., via the rational range transform manager 44) to transform the temperature from a simple string representation, such as 101.9 F, to a strongly-typed internal, floating-point representation of the value. Through associations with clinical terms and rules related to the clinical terms, the fact repository may also determine one or more attributes associated with the transformed value. For example, the fact repository may, in the foregoing example, compare the transformed temperature value to a normal range of temperature values and determine if the patient's temperature is high, normal or low. These attributes may then be stored along with or otherwise in association with the patient data.

The fact repository may then process the structured data in accordance with rules associated with clinical concepts in order to further characterize and specify the nature of the patient data. For example, the fact repository may be configured to determine trends with respect to the patient data. The definition of a trend may be dependent upon the type of patient data. For example, with respect to body temperature, three consecutive body temperature recordings above the normal range within the preceding 12 hours may define a trend that creates an additional clinical fact that may be stored in addition to the underlying patient data.

As indicated above, the fact repository may also include memory for storing the patient data, attributes related to the patient data and clinical facts that are created by analysis of the patient data. While the patient data may be stored within the memory of the fact repository while and at least shortly after the patient data is processed by the processor of the fact repository, other storage devices may also be provided, such as random access memory.

As indicated above, the database server 42 may act as a fact repository for electronically recorded clinical data regarding various activities performed with respect to a particular patient. In an exemplary embodiment, the clinical data that is written to the database server 42 may be mapped to a core-clinical ontology providing a framework for classifying the data. For example, a life-sciences ontology may be employed to provide a target representation of data for use in a patient quality monitor application. The core-clinical data may be transformed to a structured, strongly-typed form and represented as instances within the life-sciences model. Once transformed, the instances may be rationalized based on attributes such as normal, abnormal, outside normal range, within normal range, or other applicable attributes. Transformed and rationalized data may then be stored in the database server 42. In an exemplary embodiment, the database server 42 may comprise a long-term, persistent triple data store (TDS) that may be available for sending data to other applications as strongly-typed items.

Alternatively or additionally, the data stored in the database server 42 may be available for querying or searching and reporting or driving various applications. Once posted to the TDS, data can trigger or otherwise be used in connection with rule processing, including potentially complex rule processing, based on trigger mappings within the life-sciences model. As such, for example, a particular condition may be monitored by setting up rules that extract specific data from the database server 42 for use in various applications.

Figure 2:
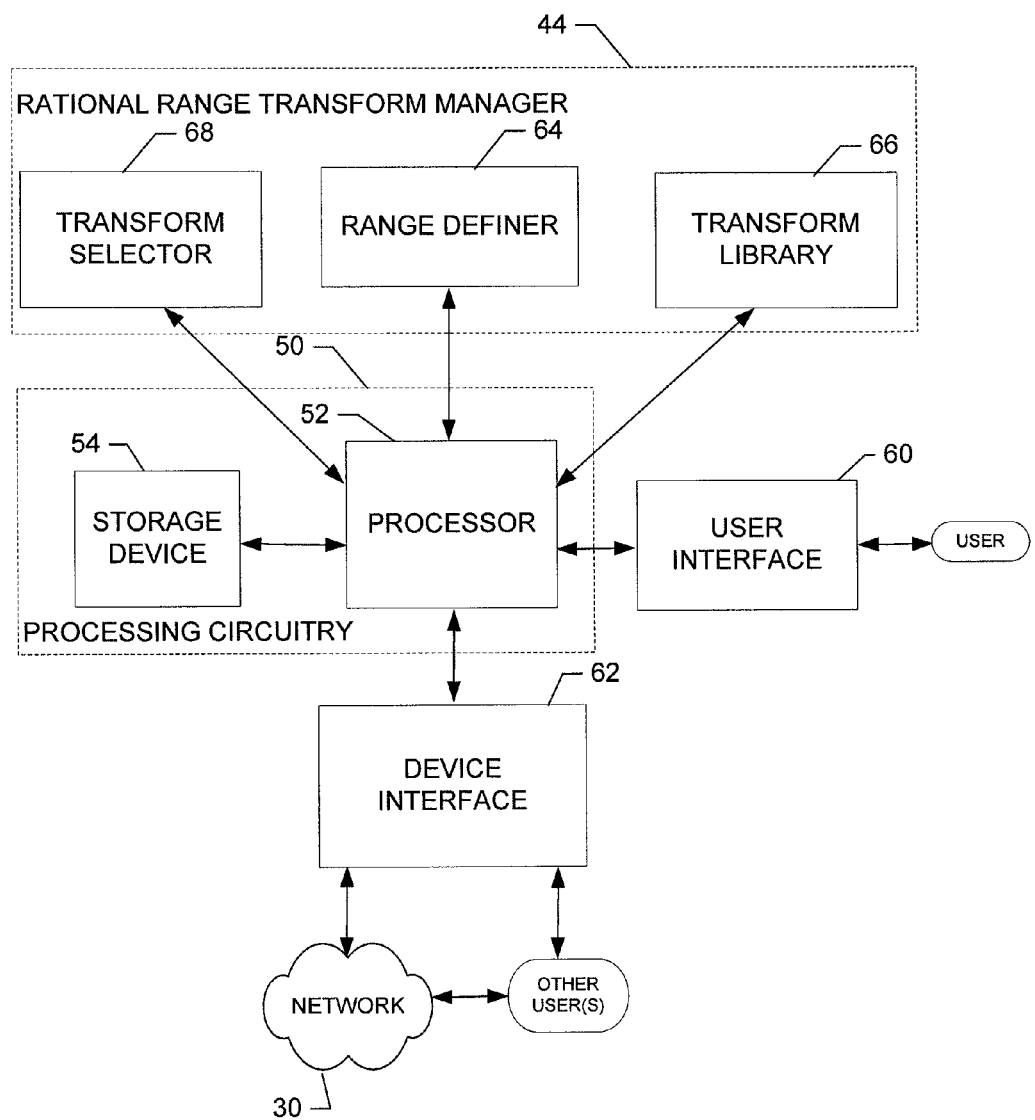
FIG. 2 is a block diagram showing various components that may be included in an apparatus for providing a rational range test for data translation according to an exemplary embodiment of the present invention.

As indicated above, the rational range transform manager 44 may provide functionality for translation of data within the network 30 to ensure that the fact repository is populated with accurate and reliable information that is up to date. An exemplary embodiment of the invention will now be described with reference to FIG. 2. FIG. 2 shows certain elements of an apparatus for providing a rational range test for data translation according to an exemplary embodiment. The apparatus of FIG. 2 may be employed, for example, on a variety of devices (such as, for example, a network device, server, proxy, or the like (e.g., the database server 42 of FIG. 1)). Alternatively, embodiments may be employed on a combination of devices. Accordingly, some embodiments of the present invention may be embodied wholly at a single device (e.g., the database server 42) or by devices in a client/server relationship (e.g., the database server 42 and one or more clients 20 or even the application server 40). Furthermore, it should be noted that the devices or elements described below may not be mandatory and thus some may be omitted in certain embodiments.

Referring now to FIG. 2, an apparatus for providing a rational range test for data translation is provided. The apparatus may include or otherwise be in communication with processing circuitry 50 that is configured to perform data processing, application execution and other processing and management services according to an exemplary embodiment of the present invention. In one embodiment, the processing circuitry 50 may include a processor 52, a storage device 54 that may be in communication with or otherwise control a user interface 60 and a device interface 62. As such, the processing circuitry 50 may be embodied as a circuit chip (e.g., an integrated circuit chip) configured (e.g., with hardware, software or a combination of hardware and software) to perform operations described herein. However, in some embodiments, the processing circuitry 50 may be embodied as a portion of a server, computer, laptop, workstation or even one of various mobile computing devices. In situations where the processing circuitry 50 is embodied as a server or at a remotely located computing device, the user interface 60 may be disposed at another device (e.g., at a computer terminal or client device such as one of the clients 20) that may be in communication with the processing circuitry 50 via the device interface 62 and/or a network (e.g., network 30).

The user interface 60 may be in communication with the processing circuitry 50 to receive an indication of a user input at the user interface 60 and/or to provide an audible, visual, mechanical or other output to the user. As such, the user interface 60 may include, for example, a keyboard, a mouse, a joystick, a display, a touch screen, a microphone, a speaker, a cell phone, or other input/output mechanisms.

The device interface 62 may include one or more interface mechanisms for enabling communication with other devices and/or networks (e.g., via the bus). In some cases, the device interface 62 may be any means such as a device or circuitry embodied in either hardware, software, or a combination of hardware and software that is configured to receive and/or transmit data from/to a network and/or any other device or module in communication with the processing circuitry 50. In this regard, the device interface 62 may include, for example, an antenna (or multiple antennas) and supporting hardware and/or software for enabling communications with a wireless communication network and/or a communication modem or other hardware/software for supporting communication via cable, digital subscriber line (DSL), universal serial bus (USB), Ethernet or other methods. In situations where the device interface 62 communicates with a network, the network may be any of various examples of wireless or wired communication networks such as, for example, data networks like a Local Area Network (LAN), a Metropolitan Area Network (MAN), and/or a Wide Area Network (WAN), such as the Internet.

In an exemplary embodiment, the storage device 54 may include one or more memory devices such as, for example, volatile and/or non-volatile memory that may be either fixed or removable. The storage device 54 may be configured to store information, data, applications, instructions or the like for enabling the apparatus to carry out various functions in accordance with exemplary embodiments of the present invention. For example, the storage device 54 could be configured to buffer input data for processing by the processor 52. Additionally or alternatively, the storage device 54 could be configured to store instructions for execution by the processor 52. As yet another alternative, the storage device 54 may include one of a plurality of databases (e.g., of the database server 42) that may store a variety of files, contents or data sets. Among the contents of the storage device 54, applications (e.g., the rational range transform manager 44) may be stored for execution by the processor 52 in order to carry out the functionality associated with each respective application.

The processor 52 may be embodied in a number of different ways. For example, the processor 52 may be embodied as various processing means such as a microprocessor or other processing element, a coprocessor, a controller or various other computing or processing devices including integrated circuits such as, for example, an ASIC (application specific integrated circuit), an FPGA (field programmable gate array), a hardware accelerator, or the like. In an exemplary embodiment, the processor 52 may be configured to execute instructions stored in the storage device 54 or otherwise accessible to the processor 52. As such, whether configured by hardware or software methods, or by a combination thereof, the processor 52 may represent an entity (e.g., physically embodied in circuitry) capable of performing operations according to embodiments of the present invention while configured accordingly. Thus, for example, when the processor 52 is embodied as an ASIC, FPGA or the like, the processor 52 may be specifically configured hardware for conducting the operations described herein. Alternatively, as another example, when the processor 52 is embodied as an executor of software instructions, the instructions may specifically configure the processor 52 to perform the operations described herein.

In an exemplary embodiment, the processor 52 (or the processing circuitry 50) may be embodied as, include or otherwise control the rational range transform manager 44, which may include, be in communication with or in some cases control a range definer 64, a transform library 66 and a transform selector 68. The example of FIG. 2 shows the range definer 64, the transform library 66 and the transform selector 68 each being a portion of the rational range transform manager 44. However, in some cases, one or more of the range definer 64, the transform library 66 and the transform selector 68 may be separate devices from the rational range transform manager 44.

The range definer 64, the transform library 66 and the transform selector 68 may each be any means such as a device or circuitry operating in accordance with software or otherwise embodied in hardware or a combination of hardware and software (e.g., processor 52 operating under software control, the processor 52 embodied as an ASIC or FPGA specifically configured to perform the operations described herein, or a combination thereof) thereby configuring the device or circuitry to perform the corresponding functions of the range definer 64, the transform library 66 and the transform selector 68, respectively, as described below.

In an exemplary embodiment, the rational range transform manager 44 may be configured to listen to the bus (e.g., via the device interface 62) for data on the bus that needs alteration or translation. In response to detecting data for altering or translating, the rational range transform manager 44 may process the detected data according to a rational range defined for the detected data by the range definer 64 using a selected transform selected by the transform selector 68 from among a collection of potential transforms stored in the transform library 66. As such, the range definer 64, the transform library 66 and the transform selector 68 may provide a mechanism to "train" the rational range transform manager 44 to translate the detected data for provision to, and perhaps storage at, the fact repository. As such, the rational range transform manager 44 of an exemplary embodiment is configured to map a local concept to a universal concept. As an example, a local concept may have a free text response or string such as a temperature reading value of "98.6" or a blood pressure entry such as "120/80". The rational range transform manager 44 may be configured to translate the entered string (e.g., "98.6") into a numerical value for storage in the fact repository (e.g., as a number 98.6). When translating more complex strings (e.g., "120/80"), the rational range transform manager 44 may be configured to provide a translation of a corresponding number of numeric values (e.g., two numeric values such as 120 for systolic and 80 for diastolic).

In many situations, the data detected on the bus may include variations. Moreover, the types of variations that may be encountered are, in some cases, different and distinctive for each organization. In this regard, due to the conventions or standard practices that are in place in any given organization, certain types of errors and variations may be more common than others. Accordingly, it may be beneficial to train the rational range transform manager 44 to provide for utilization of a selected one from among a plurality of potential transforms that may be employed. Furthermore, it may be desirable to provide a mechanism to train the rational range transform manager 44 to select an optimal, "best" or otherwise desirable transform based on an analysis of common data encountered at the organization. As such, according to an exemplary embodiment, the rational range transform manager 44 may be trained using the range definer 64, the transform library 66 and the transform selector 68 such that the rational range transform manager 44 is essentially tuned to the organization in which it operates.

For many types of data (e.g., blood pressure readings, temperature readings, lab results, etc.) there is a physiologic limit to the values that may be encountered. In this regard, for example, beyond the "normal" range of healthy human body temperatures, there are limits to the highest and lowest temperatures that may be expected to be encountered in living humans. These physiologic limits may define a rational range of values that are "rational", believable or otherwise acceptable for data corresponding to such measurements. In an exemplary embodiment, the range definer 64 may store (e.g., in a database or other memory device such as storage device 54) information defining a rational range for each of various different types of information. In many cases, the rational ranges of the range definer 64 may be fixed and predetermined values. However, in some cases, a user may alter values associated with defining rational ranges for one or more of the different types of information that may be encountered. Accordingly, the rational range transform manager 44 may be configured to reference the range definer 64 to determine rational ranges for data detected by the rational range transform manager 44. While the rational range transform manager 44 may only reference the range definer 64 during the training operation sequence in some embodiments, the rational range transform manager 44 could alternatively be configured to reference the range definer 64 during both training and operation sequences. In this regard, for example, while the range definer 64 is typically used in connection with a rational range test during the training operation sequence to define transform rules, the range definer 64 could also be referenced during the normal operation sequence (e.g., at run time) in order to identify values that can be classified as "bad data".

The transform library 66 may store (e.g., in a database or other memory device such as storage device 54) a plurality of potential transforms that may be used to transform a particular type of data. As such, for each different type of data, the transform library 66 may store a plurality of different transforms (e.g., transform rules) that may be selected. Each of the transforms in the transform library 66 may define corresponding transform rules for translating detected data into translated data for storage at the fact repository. The transform rules may define an action (or actions) to be taken in response to a particular stimulus. Thus, for example, if data is encountered in a particular form, a transform rule may provide direction as to how to modify the data.

In an exemplary embodiment, the transform library 66 may include one or more potential transforms for each of various different data types. As such, each potential transform (or candidate transform) in the transform library 66 may correspond to a particular type of information and the corresponding rational range that applies to that particular type of information as determined during the training operation sequence by application of a rational range test using the range definer 64. The potential transforms may be predefined transforms or transforms that are user defined or may be modified by the user (e.g., via the user interface 60). In some cases, the translation rules may operate with respect to values inside or outside the rational range. However, in other cases, some translation rules may apply to values regardless of whether such values are inside or outside the rational range.

Thus, the transform library 66 and the range definer 64 may be utilized for providing transform rules and rational ranges for various different types of data. In order to tailor the transform to ultimately be used for translation of incoming data, the transform selector 68 may be employed to train the rational range transform manager 44 for translation during normal operation. To train the rational range transform manager 44, the transform selector 68 may be provided with a set of data that corresponds to real data associated with a particular organization at which the rational range transform manager 44 is to operate. Since the real data is data actually entered by personnel at the particular organization, the real data can be expected to include variations and/or errors that are typical of the particular organization based on the conventions and procedures that may be unique to the particular organization. The transform selector 68 may then analyze the real data provided and select an appropriate transform from the transform library 66 for the particular organization. The selected transform may then be used on future incoming data to translate such data for provision of the translated data to the fact repository.

The transform selector 68 may be configured to select a transform from among potential transforms in the transform library 66. In an exemplary embodiment, the transform selector 68 may be configured to apply multiple transforms from the transform library 66 to a set of data (e.g., real data) from the particular organization. Results of translation for each transform applied may then be compared to determine which transform to use based on the transform results. In some cases, the transform that supplied the highest number of results that fall within the rational range may be selected by the transform selector 68 for future use by the rational range transform manager 44. As such, during the training operation sequence, the rational range transform manager 44 may perform one or more rational range tests in order to select a corresponding transform rule to be applied to each corresponding type of data likely to be encountered during runtime. Thereafter, during runtime in the normal operation sequence, the selected transform rules are applied to respective types of data to transform each type as appropriate for the particular organization.

Table 1 below provides an example table that illustrates operation of the transform selector 68 according to an exemplary embodiment. In this regard, Table 1 proves an example of translation using two different example potential transforms (referred to as regular expressions (Reg Ex 1 and Reg Ex 2). In this regard, the far left column illustrates patient result values (e.g., PAT_RESULTS Values) indicative of example entries of data from a set of real data for an organization for which the rational range transform manager 44 is being trained to operation. For this example, the type of data being transformed is assumed to be human body temperature. Accordingly, the second column (moving from left to right) provides the rational range for human body temperature, which is defined in this example to extend from 90 degrees Fahrenheit to 110 degrees Fahrenheit. In some cases, an error value may be assigned to extend the allowable values considered for translation relative to the rational range such as by applying a particular percentage (e.g., 5%) to the boundaries of the rational range.

The third column (again moving from left to right) provides a human translation. Although not required during operation, the human translation value of Table 1 illustrates how a human translator can generally reason that even some values that appear to fit a format indicative of a value that falls in the rational range may not actually fall within the range. In this regard, a human may interpret the real data relative to the rational range and provide a corresponding translation that may be assumed to be correct as the human may be able to determine accurately the appropriate translation for those values that are rational with respect to the type of data being transformed. The fourth and fifth columns from the left then show the results of application of the translation rules defined for Reg Ex 1 and Reg Ex 2, respectively. Table 1 is as follows:

TABLE 1

Translation of temperature strings

| PAT_RESULTS Value | Rational range | Human translation | Reg Ex 1 | Reg Ex 2 |
|---|---|---|---|---|
| 98.6 | 90-110 | 98.6 | 98 | 98.6 |
| 9 | 90-110 | — | | |
| 1033 | 90-110 | — | | |
| 103 Oral F | 90-110 | 103 | | |
| Patient refused | 90-110 | — | — | — |
| 73 | 90-110 | — | | |
| 96.8 | 90-110 | 96.8 | 96 | 96.8 |
| 144/87 | 90-110 | — | | |
| 98.7 RE, 98.9 LE | 90-110 | 98.7 | 98 | 98.7 |
| 98/63 | 90-110 | — | 98 | 98 |
| Percent in rational range (of 10) | | | 40% | 50% |

As shown in Table 1, the text strings provided in the PAT_RESULTS Value column appear to include some values that are recognizable as patient temperature values based on the rational range defined for human body temperature, and those values are indicated as such in the human translation column. However, some of the other values include text strings that would appear to correspond to blood pressure readings or other unknown values. Meanwhile, the translation results for each of Reg Ex 1 and Reg Ex 2 are also included in their corresponding columns.

In this example, Reg Ex 1 may include the following simple translation rule: change the first two characters to a numeric value. Meanwhile, Reg Ex 2 may include the following simple translation rule: use all initial characters (from left to right) until the end of the string or until the first alphabetical character is encountered and convert characters prior to the first alphabetical character (or all characters if the end of the string is reached without an alphabetic character) to numeric values. In columns four and five, the results of the application of each corresponding transform (e.g., the application of the corresponding transform rule) are shown. In operation, the transform selector 68 discounts or deletes values that fall outside of the rational range (as indicated by the values that are lined through in Table 1). After providing each translated result and discounting those values that lie outside the rational range, the transform selector 68 may be configured to compare the percentage of values that fall in the rational range for each potential transform. In the present example, Reg Ex 1 provided translation results for which 40% of the results fell inside the rational range while Reg Ex 2 provided translation results for which 50% of the results fell inside the rational range. Thus, for this example, the transform selector 68 may select Reg Ex 2. When the rational range transform manager 44 detects data to be translated thereafter, the rational range transform manager 44 may apply the selected transform rule (e.g., Reg Ex 2 in this example) to the detected data for translation thereof.

In an exemplary embodiment, a user may be asked to verify the selected transform rule. However, in other fully automated examples, no human intervention may be needed at all. In examples where human review is utilized, a user interface (perhaps similar to Table 1) may be provided to show the translated results (or a sample set of translated results) of one (e.g., the selected transform) or more transforms. The user may then be enabled to compare the results of the transforms, review the percentage of results that fell in the rational range and/or perform human translations to compare the accuracy of the results or the transforms to the human translations. The user may then determine whether the error rate is acceptable and/or whether the selected transform should be used. The user could, if desired, manually select a different transform for use.

In an exemplary embodiment, other than being used to translate data during runtime (e.g., apply the selected transform rule to incoming data for storage at the fact repository), some embodiments of the present invention could also or alternatively be used for making quality or other data interpretations. In relation to quality determinations, data that has been transformed may be routinely, periodically, or specifically selected by a user for re-interpretation using, for example, an alternative transform. As such, for example, data transformed over a period of time using a selected transform may be analyzed with other transforms to determine whether the data may be more accurately translated using a different transform. In this regard, transform results by one or more other potential transforms (or even a specialized evaluation transform including an algorithm configured to test the effectiveness or accuracy of another transform) may be employed and the original transform results may be compared to the results generated by the one or more other potential transforms to determine the relative accuracy between the different transforms (e.g., by determining which transform provides more results within the rational range). In other words, in addition to training and normal operation sequences as described above, an additional operation sequence such as a feedback or evaluation operation sequence may also be provided by the rational range transform manager 44 in order to update transform rules as appropriate or desired. In such examples, the rational range test may be reapplied after several runtime examples have been encountered to evaluate effectiveness of the selected transform rules.

While the rational range test is typically only employed during the training operation sequence in order to generate selected transform rules (or perhaps during feedback or evaluation operation sequences to evaluate modifying previously selected transform rules), in another example, a rational range test may be performed at runtime to guide interpretation of data that falls outside of the rational range. Data that falls outside the rational range may then be selectively discarded and replaced with a missing data point indicator, presented as a suspicious value (e.g., with a warning regarding the dubious nature of the corresponding value), post-processed by one or more algorithms or other data processing techniques to attempt to convert the data to a likely value within range, used without warning or feedback, and/or treated in some other fashion.

Some embodiments of the present invention may therefore enable organizations to have translation of data performed in a manner that is tailored to the specific conventions and/or procedures employed by the respective organizations. In this regard, for example, a predetermined library of transforms may be provided to an organization and the organization may use data provided by personnel of the organization in order to train a rational range transform manager 44 to transform input strings of free text into useable data (e.g., of a format useable for software applications that process such data) for storage in a fact repository. The training may include the selection of one among a plurality of potential transforms in a library of transforms based on a comparison of the accuracy of the transforms in terms of producing results that fall within a rational range for the corresponding type of data (e.g., the corresponding particular physiologic patient data being translated).

Figure 3:
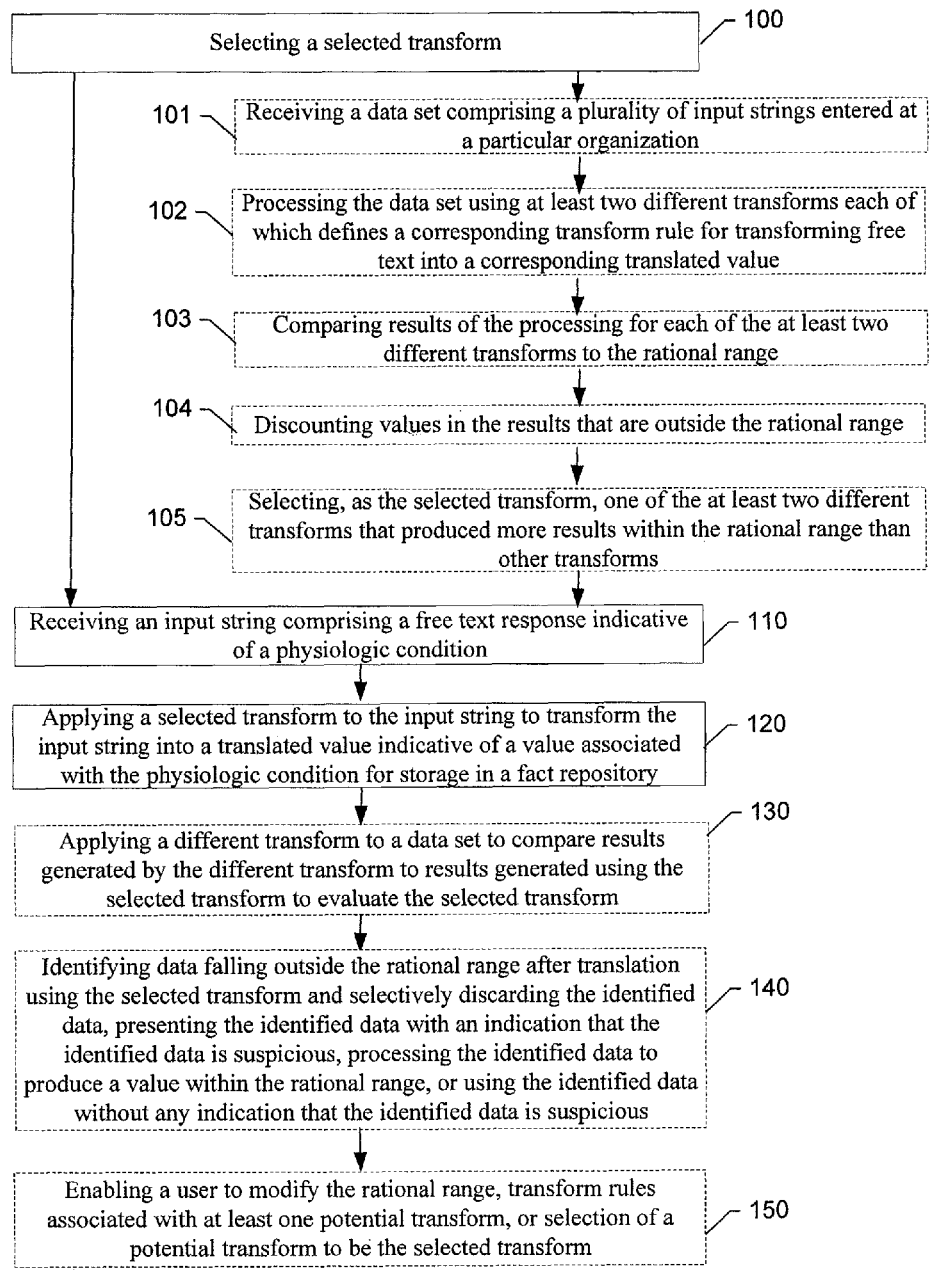
FIG. 3 is a block diagram according to an exemplary method for providing a data translation according to an exemplary embodiment of the present invention.

Embodiments of the present invention may therefore be practiced using an apparatus such as the one depicted in FIG. 2. However, other embodiments may be practiced in connection with a computer program product for performing embodiments of the present invention. FIG. 3 is a flowchart of a method and program product according to exemplary embodiments of the invention. Each block or step of the flowchart of FIG. 3, and combinations of blocks in the flowchart, may be implemented by various means, such as hardware, firmware, processor, circuitry and/or another device associated with execution of software including one or more computer program instructions. Thus, for example, one or more of the procedures described above may be embodied by computer program instructions, which may embody the procedures described above and may be stored by a storage device (e.g., storage device 54) and executed by processing circuitry (e.g., processor 52).

As will be appreciated, any such stored computer program instructions may be loaded onto a computer or other programmable apparatus (i.e., hardware) to produce a machine, such that the instructions which execute on the computer or other programmable apparatus implement the functions specified in the flowchart block(s) or step(s). These computer program instructions may also be stored in a computer-readable medium comprising memory that may direct a computer or other programmable apparatus to function in a particular manner, such that the instructions stored in the computer-readable memory produce an article of manufacture including instructions to implement the function specified in the flowchart block(s) or step(s). The computer program instructions may also be loaded onto a computer or other programmable apparatus to cause a series of operational steps to be performed on the computer or other programmable apparatus to produce a computer-implemented process such that the instructions which execute on the computer or other programmable apparatus provide steps for implementing the functions specified in the flowchart block(s) or step(s).

In this regard, a method according to one embodiment of the invention, as shown in FIG. 3, may include receiving an input string comprising a free text response indicative of a physiologic condition at operation 110, and applying a selected transform to the input string to transform the input string into a translated value indicative of a value associated with the physiologic condition for storage in a fact repository at operation 120. The selected transform may be selected from a library of potential transforms based on results of the selected transform relative to a rational range associated with the physiologic condition.

In some cases, the method may include additional optional operations, examples of which are shown in dashed lines in FIG. 3. In this regard, in an exemplary embodiment, the method may further include selecting the selected transform prior to receiving the input string at operation 100. In some embodiments, selecting the selected transform may include several sub-operations that are performed before runtime in a training operation sequence. As an example, in some cases, selecting the selected transform may include receiving a data set comprising a plurality of input strings entered at a particular organization at operation 101, processing the data set using at least two different transforms each of which defines a corresponding transform rule for transforming free text into a corresponding translated value at operation 102, comparing results of the processing for each of the at least two different transforms to the rational range at operation 103, and discounting (e.g., deleting or otherwise ignoring or identifying as incorrect) values in the results that are outside the rational range at operation 104. In some embodiments, the sub-operations may further include selecting, as the selected transform, one of the at least two different transforms that produced more results within the rational range than other transforms at operation 105.

In another exemplary embodiment, the method may also or alternatively include applying a different transform to a data set to compare results generated by the different transform to results generated using the selected transform to evaluate the selected transform at operation 130. As an alternative to operation 130 (or in addition thereto), the method may also include identifying data falling outside the rational range after translation using the selected transform and selectively discarding the identified data, presenting the identified data with an indication that the identified data is suspicious, processing the identified data to produce a value within the rational range, and/or using the identified data without any indication that the identified data is suspicious at operation 140. Another possible alternative or additional operation may include enabling a user to modify the rational range, transform rules associated with at least one potential transform, or selection of a potential transform to be the selected transform at operation 150. Other modifications are also possible.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A method for providing a data translation comprising:
   selecting a transform by receiving a data set comprising a plurality of input strings entered at a particular organization, processing the data set using at least two different transforms each of which defines a corresponding transform rule for transforming free text into a corresponding translated value, comparing results of the processing for each of the at least two different transforms to the rational range, discounting values in the results that are outside the rational range, and selecting, as the selected transform, one of the at least two different transforms that produced more results within the rational range than other transforms;
   receiving an input string comprising a free text response indicative of a physiologic condition, wherein the free text response is entered by personnel at the organization; and
   applying the selected transform to the input string, with a processor, to transform the input string into a translated value indicative of a value associated with the physiologic condition for storage in a fact repository, wherein applying the selected transform comprises transforming an initial representation of the input string to the translated value in a standard form of representation,
   wherein the selected transform is selected from a library of potential transforms by applying the at least two different transforms from the library to the data set and selecting the selected transform from among the library of potential transforms based on results of the selected transform applied to the data set encountered at the respective organization relative to the rational range defined by physiologic limits associated with the physiologic condition and in comparison to results obtained by application of other transforms from the library to the data set.

2. The method of claim 1, wherein the selected transform is selected prior to receiving the input string.

3. The method of claim 1, further comprising applying a different transform to a data set to compare results generated by the different transform to results generated using the selected transform to evaluate the selected transform.

4. The method of claim 1, further comprising identifying data falling outside the rational range after translation using the selected transform and selectively:
   discarding the identified data;
   presenting the identified data with an indication that the identified data is suspicious;
   processing the identified data to produce a value within the rational range; or using the identified data without any indication that the identified data is suspicious.

5. The method of claim 1, further comprising enabling a user to modify the rational range, transform rules associated with at least one potential transform, or selection of a potential transform to be the selected transform.

6. A computer program product for providing a data translation, the computer program product comprising at least one non-transitory computer-readable storage medium having computer-executable program code instructions stored therein, the computer-executable program code instructions comprising:

program code instructions for selecting a transform by receiving a data set comprising a plurality of input strings entered at a particular organization, processing the data set using at least two different transforms each of which defines a corresponding transform rule for transforming free text into a corresponding translated value, comparing results of the processing for each of the at least two different transforms to the rational range, discounting values in the results that are outside the rational range, and selecting, as the selected transform, one of the at least two different transforms that produced more results within the rational range than other transforms;

program code instructions for receiving an input string comprising a free text response indicative of a physiologic condition, wherein the free text response is entered by personnel at the organization; and program code instructions for applying the selected transform to the input string to transform the input string into a translated value indicative of a value associated with the physiologic condition for storage in a fact repository, wherein the program code instructions for applying the selected transform comprise program code instructions for transforming an initial representation of the input string to the translated value in a standard form of representation, wherein the selected transform is selected from a library of potential transforms by applying the at least two different transforms from the library to the data set and selecting the selected transform from among the library of potential transforms based on results of the selected transform applied to the data set encountered at the respective organization relative to the rational range defined by physiologic limits associated with the physiologic condition and in comparison to results obtained by application of other transforms from the library to the data set.

7. The computer program product of claim 6, wherein the selected transform is selected prior to receiving the input string.

8. The computer program product of claim 6, further comprising program code instructions for applying a different transform to a data set to compare results generated by the different transform to results generated using the selected transform to evaluate the selected transform.

9. The computer program product of claim 6, further comprising program code instructions for identifying data falling outside the rational range after translation using the selected transform and selectively:

discarding the identified data;
presenting the identified data with an indication that the identified data is suspicious;
processing the identified data to produce a value within the rational range; or
using the identified data without any indication that the identified data is suspicious.

10. The computer program product of claim 6, further comprising program code instructions for enabling a user to modify the rational range, transform rules associated with at least one potential transform, or selection of a potential transform to be the selected transform.

11. An apparatus comprising processing circuitry configured to:

select a transform by receiving a data set comprising a plurality of input strings entered at a particular organization, process the data set using at least two different transforms each of which defines a corresponding transform rule for transforming free text into a corresponding translated value, compare results of the processing for each of the at least two different transforms to the rational range, discount values in the results that are outside the rational range, and select, as the selected transform, one of the at least two different transforms that produced more results within the rational range than other transforms;

receive an input string comprising a free text response indicative of a physiologic condition, wherein the free text response is entered by personnel at the organization; and apply the selected transform to the input string to transform the input string into a translated value indicative of a value associated with the physiologic condition for storage in a fact repository, wherein the processing circuitry is configured to apply the selected transform by transforming an initial representation of the input string to the translated value in a standard form of representation, wherein the selected transform is selected from a library of potential transforms by applying the at least two different transforms from the library to the data set and selecting the selected transform from among the library of potential transforms based on results of the selected transform applied to the data set encountered at the respective organization relative to the rational range defined by physiologic limits associated with the physiologic condition and in comparison to results obtained by application of other transforms from the library to the data set.

12. The apparatus of claim 11, wherein the selected transform is selected prior to receiving the input string.

13. The apparatus of claim 11, wherein the processing circuitry is further configured to apply a different transform to a data set to compare results generated by the different transform to results generated using the selected transform to evaluate the selected transform.

14. The apparatus of claim 11, wherein the processing circuitry is further configured to enable a user to modify the rational range, transform rules associated with at least one potential transform, or selection of a potential transform to be the selected transform.

* * * * *